United States Patent
Concibido et al.

(10) Patent No.: US 11,457,590 B2
(45) Date of Patent: Oct. 4, 2022

(54) BUTTERFLY PEA VARIETY SXT BFP

(71) Applicant: Sensient Colors, LLC, St. Louis, MO (US)

(72) Inventors: Vergel C. Concibido, Maryland Heights, MO (US); Jöerg Meyer, St. Charles, MO (US)

(73) Assignee: SENSIENT COLORS, LLC, Saint Louis, MO (US)

( * ) Notice: Subject to any disclaimer, the term of this patent is extended or adjusted under 35 U.S.C. 154(b) by 219 days.

(21) Appl. No.: 16/570,477

(22) Filed: Sep. 13, 2019

(65) Prior Publication Data

US 2020/0084991 A1 Mar. 19, 2020

Related U.S. Application Data

(60) Provisional application No. 62/730,930, filed on Sep. 13, 2018.

(51) Int. Cl.
*A01H 6/54* (2018.01)
*A01H 5/02* (2018.01)

(52) U.S. Cl.
CPC ............... *A01H 6/54* (2018.05); *A01H 5/02* (2013.01)

(58) Field of Classification Search
None
See application file for complete search history.

(56) References Cited

PUBLICATIONS

Lakshan et al 2020 (Ceylon Journal of Science 49:2, p. 195-201) (Year: 2020).*
Gomez, S. et al., "Butterfly Pea (*Clitoria ternatea*): A Nutritive Multipurpose Forage Legume for the Tropics—An Overview", Pakistan J Nutrition, 2(6):374-9, (2003).
Kazuma, K. et al., "Malonylated Flavonol Glycosides from the Petals of Clitoria Ternatea", Phytochemistry, 62(2):229-37, (2003).
Morris, J., "Characterization of Butterfly Pea (*Clitoria ternatea* L.) Accessions for Morphology, Phenology, Reproduction and Potential Nutraceutical, Pharmaceutical Trait Utilization", Genet Resour Crop Evol., 56:421-7, (2009).
Mukherjee, P. et al., "The Ayurvedic Medicine Clitoria Ternatea—From Traditional Use to Scientific Assessment", J Ethnopharmacol., 120(3):291-301, (2008).
Terahara, N. et al., "Acylated Anthocyanins of Clitoria Ternatea Flowers and their Acyl Moieties", Phytochemistry, 29(3):949-53, (1990).

* cited by examiner

*Primary Examiner* — Matthew R Keogh
(74) *Attorney, Agent, or Firm* — Quarles & Brady, LLP

(57) ABSTRACT

The invention relates to the butterfly pea variety designated SXT BFP. Provided by the invention are the seeds, plants and derivatives of the butterfly pea variety SXT BFP. Also provided by the invention are tissue cultures of the butterfly pea variety SXT BFP and the plants regenerated therefrom. Still further provided by the invention are methods for producing butterfly pea plants by crossing the butterfly pea variety SXT BFP with itself or another butterfly pea variety and plants produced by such methods.

16 Claims, 4 Drawing Sheets

FIG. 1

| Sample Number | Accession | Origin | | | Plant Height (cm) | Leaf Length (cm) | Leaf Width (cm) | Flower Length (cm) | Flower Width (cm) | Calix Length (cm) | Weight of 1 Fresh Flower (gram) | Estimated Weights of 100 Fresh Flower (gram) | Weights of Fresh Flower per Plant (gram) | Weight of Total Fresh Flower (gram) |
|---|---|---|---|---|---|---|---|---|---|---|---|---|---|---|
| | | | Province | District | | | | | | | | | | |
| 66 | 209315 USDA | | U.S Virgin Islands | | 89.44 | 3.23 | 2.20 | 4.98 | 3.85 | 2.27 | 0.31 | 24.14 | 4.02 | 67.73 |
| 67 | 209591 USDA | | Cuba | | 101.02 | 3.83 | 2.32 | 5.83 | 3.98 | 2.62 | 0.40 | 40.19 | 5.60 | 96.68 |
| 68 | 209592 USDA | | Cuba | | 43.10 | 3.58 | 2.25 | 2.78 | 1.95 | 1.18 | 0.23 | 52.07 | 4.90 | 82.36 |
| 70 | 226265 USDA | | Kenya | | 96.18 | 3.57 | 2.42 | 5.18 | 3.47 | 2.22 | 0.37 | 22.06 | 1.64 | 79.72 |
| 71 | 258379 USDA | | Taiwan | | 107.92 | 3.05 | 1.93 | 5.27 | 3.97 | 2.33 | 0.19 | 38.82 | 4.20 | 35.15 |
| 72 | 283231 USDA | | Sudan | | 143.57 | 3.56 | 2.14 | 5.40 | 4.60 | 2.52 | 0.28 | 31.47 | 6.35 | 144.39 |
| 73 | 320977 USDA | | Sierre Leone | | 119.58 | 3.67 | 2.22 | 5.82 | 4.02 | 2.63 | 0.38 | 27.36 | 7.32 | 114.13 |
| 74 | 295357 USDA | | Taiwan | | 56.63 | 3.52 | 2.20 | 2.60 | 1.83 | 1.08 | 0.21 | 11.43 | 1.90 | 35.66 |
| 75 | 311506 USDA | | Brazil | | 181.70 | 3.23 | 2.19 | 5.28 | 4.03 | 2.50 | 0.41 | 27.40 | 4.63 | 196.34 |
| 76 | 316204 USDA | | Australia | | 79.15 | 2.90 | 1.83 | 5.03 | 3.90 | 2.42 | 0.11 | 4.50 | 1.63 | 30.42 |
| 77 | 319465 USDA | | Tanzania | | 45.20 | 2.53 | 1.57 | 2.33 | 1.67 | 1.27 | 0.13 | 6.82 | 1.25 | 5.75 |
| 78 | 283232 USDA | | Sierre Leone | | 105.95 | 3.31 | 2.17 | 5.47 | 3.80 | 2.33 | 0.37 | 38.10 | 9.33 | 129.84 |
| 79 | 322364 USDA | | Brazil | | 72.50 | 2.91 | 1.86 | 2.78 | 1.73 | 0.98 | 0.18 | 24.34 | 4.56 | 42.13 |
| 80 | 451721 USDA | | Mexico | | 82.90 | 2.80 | 1.97 | 5.63 | 3.97 | 2.35 | 0.44 | 6.01 | 4.30 | 73.60 |
| 81 | 538311 USDA | | Dominican Republic | | 172.30 | 3.52 | 2.23 | 5.63 | 3.98 | 2.42 | 0.37 | 23.34 | 3.52 | 55.48 |
| 82 | 641948 USDA | | U.S Virgin Islands | | 103.48 | 3.19 | 1.85 | 5.42 | 4.03 | 1.90 | 0.38 | 11.52 | 2.52 | 68.01 |
| 85 | SXT BFP | | Thailand | Thailand | 63.80 | 2.65 | 1.77 | 2.45 | 1.60 | 0.90 | 0.18 | 14.68 | 4.41 | 21.14 |

FIG. 1 (continued)

| Sample Number | Accession | Origin | | Flower Color | Petal Number | Leaf Shape | Growth Habit | Pod Length (cm) | Pod Width (mm) | Number Of Pod per Plant | Weight of pods per plant (gram) | Number Of Total Pods | Weight of total pods (gram) |
|---|---|---|---|---|---|---|---|---|---|---|---|---|---|
| | | Province | District | | | | | | | | | | |
| 66 | 209315 USDA | U.S Virgin Islands | | 3 | 1 | 5 | 1 | 10.83 | 9.02 | 78.33 | 78.12 | 586.25 | 582.64 |
| 67 | 209591 USDA | Cuba | | 8 | 1 | 2 | 2 | 10.10 | 8.08 | 109.58 | 83.32 | 547.92 | 416.59 |
| 68 | 209592 USDA | Cuba | | 7 | 1 | 5 | 1 | 4.98 | 4.38 | 52.50 | 42.25 | 525.00 | 422.48 |
| 70 | 226265 USDA | Kenya | | 6 | 1 | 5 | 1 | 9.99 | 7.83 | 132.17 | 80.90 | 872.50 | 536.08 |
| 71 | 258379 USDA | Taiwan | | 7 | 1 | 4 | 2 | 11.49 | 9.58 | 138.25 | 132.76 | 607.50 | 663.81 |
| 72 | 283231 USDA | Sudan | | 3 | 1 | 5 | 2 | 11.30 | 9.53 | 167.50 | 149.46 | 837.50 | 747.30 |
| 73 | 320977 USDA | Sierre Leone | | 1 | 1 | 5 | 1 | 10.18 | 9.13 | 197.50 | 172.39 | 987.50 | 861.93 |
| 74 | 295357 USDA | Taiwan | | 5 | 1 | 4 | 2 | 5.93 | 5.04 | 51.75 | 48.19 | 517.50 | 481.90 |
| 75 | 311506 USDA | Brazil | | 5 | 1 | 5 | 2 | 10.23 | 8.73 | 216.33 | 178.81 | 1622.50 | 1341.08 |
| 76 | 316204 USDA | Australia | | 1 | 1 | 5 | 2 | 10.25 | 8.92 | 96.00 | 107.77 | 480.00 | 538.85 |
| 77 | 319465 USDA | Tanzania | | 2 | 1 | 1 | 2 | 4.47 | 4.25 | 23.00 | 13.37 | 230.00 | 133.65 |
| 78 | 283232 USDA | Sierre Leone | | 4 | 1 | 1 | 2 | 10.69 | 9.11 | 164.67 | 134.86 | 1127.92 | 930.87 |
| 79 | 322364 USDA | Brazil | | 7 | 1 | 1 | 2 | 10.58 | 8.41 | 60.25 | 47.67 | 301.25 | 238.34 |
| 80 | 451721 USDA | Mexico | | 2 | 1 | 4 | 2 | 9.78 | 9.40 | 128.83 | 110.21 | 266.67 | 214.41 |
| 81 | 538311 USDA | Dominican Republic | | 7 | 1 | 2 | 2 | 10.54 | 9.25 | 179.17 | 148.10 | 766.25 | 590.50 |
| 82 | 641948 USDA | U.S Virgin Islands | | 4 | 1 | 5 | 2 | 19.55 | 14.95 | 113.67 | 101.35 | 700.00 | 625.91 |
| 85 | SXT BFP | Thailand | | 2 | 2 | 1 | 1 | 3.83 | 5.10 | 12.00 | 7.10 | 120.00 | 70.95 |

FIG. 1 (continued)

| Sample Number | Accession | Origin | | | Seed Length (mm) | Seed Width (mm) | Seed Diameter (mm) | Number of seed per pod | Weight of seed per plant (gram) | Weight of 100 seed (gram) | Weight of total seed (gram) |
|---|---|---|---|---|---|---|---|---|---|---|---|
| | | | Province | District | | | | | | | |
| 66 | 209315 | USDA | U.S Virgin Islands | | 5.91 | 3.75 | 2.41 | 9.22 | 36.36 | 5.97 | 268.45 |
| 67 | 209591 | USDA | Cuba | | 6.40 | 3.57 | 2.28 | 6.72 | 42.82 | 5.12 | 214.10 |
| 68 | 209592 | USDA | Cuba | | 2.85 | 1.80 | 0.95 | 2.72 | 22.49 | 2.96 | 224.88 |
| 70 | 226265 | USDA | Kenya | | 5.52 | 3.58 | 2.30 | 5.50 | 47.78 | 3.59 | 238.90 |
| 71 | 258379 | USDA | Taiwan | | 5.85 | 3.87 | 2.38 | 6.61 | 62.48 | 5.47 | 312.38 |
| 72 | 283231 | USDA | Sudan | | 5.06 | 3.13 | 1.94 | 6.06 | 65.51 | 5.09 | 327.54 |
| 73 | 320977 | USDA | Sierre Leone | | 5.60 | 3.78 | 2.07 | 5.89 | 86.51 | 5.31 | 432.53 |
| 74 | 295357 | USDA | Taiwan | | 3.13 | 1.96 | 0.96 | 3.28 | 23.49 | 3.37 | 234.88 |
| 75 | 311506 | USDA | Brazil | | 5.46 | 3.81 | 2.04 | 8.83 | 135.21 | 5.26 | 676.04 |
| 76 | 316204 | USDA | Australia | | 5.38 | 3.58 | 1.95 | 3.33 | 57.96 | 5.65 | 289.78 |
| 77 | 319465 | USDA | Tanzania | | 2.72 | 1.88 | 1.12 | 3.67 | 6.34 | 1.84 | 63.40 |
| 78 | 283232 | USDA | Sierre Leone | | 6.22 | 4.37 | 2.55 | 9.94 | 89.05 | 5.41 | 584.14 |
| 79 | 322364 | USDA | Brazil | | 6.24 | 4.17 | 2.66 | 5.61 | 21.93 | 5.41 | 109.64 |
| 80 | 451721 | USDA | Mexico | | 4.69 | 2.98 | 1.88 | 5.94 | 59.60 | 5.33 | 297.98 |
| 81 | 538311 | USDA | Dominican Republic | | 5.29 | 3.73 | 1.87 | 8.11 | 95.58 | 5.64 | 477.88 |
| 82 | 641948 | USDA | U.S Virgin Islands | | 6.28 | 3.92 | 2.23 | 8.19 | 55.90 | 5.76 | 279.48 |
| 85 | SXT BFP | | Thailand | Thailand | 2.73 | 2.18 | 1.07 | 3.67 | 2.36 | 3.41 | 23.55 |

FIG. 2

| | | | |
|---|---|---|---|
| Flower color | 1 | RHS N89A | Use royal horticultural society colour chart |
| | 2 | RHS 93A | |
| | 3 | RHS 95 A | |
| | 4 | RHS 96 B | |
| | 5 | RHS 94 A | |
| | 6 | RHS 97 A | |
| | 7 | RHS N89B | |
| | 8 | RHS 155 D | |
| Petal Number | 1 | Single petal | |
| | 2 | Double petal | |
| Leaf Shape | 1 | Elliptic | |
| | 2 | Acute | |
| | 3 | Lancolate | |
| | 4 | Obtuse | |
| | 5 | Ovale | |
| Growth Habit | 1 | Determinate | |
| | 2 | Indeterminate | |

BUTTERFLY PEA VARIETY SXT BFP

This application claims the benefit of priority of United States Provisional Application No. 62/730,930, filed Sep. 13, 2018, the disclosure of which is hereby incorporated by reference as if written herein in its entirety.

FIELD OF THE INVENTION

The present invention relates to the field of plant breeding. In particular, the invention provides butterfly pea plants with a high anthocyanin level in the flowers. The invention further provides for a new and distinct butterfly pea variety SXT BFP and for breeding methods with these plants.

BACKGROUND OF THE INVENTION

Butterfly pea, *Clitoria ternatea* (L.), is a plant species belonging to the Fabaceae family, Phaseoleae tribe, and Clitoriinae subtribe, found in many countries worldwide. Butterfly pea has a diploid chromosome number of 2n=16. The plant is tall, slender, climbing herbaceous vine with five leaflets, white to purple flowers, and has deep roots. The flowers of this vine were imagined having the shape of human female genitals, hence the Latin name of the genus "*Clitoria*", from "clitoris". Butterfly pea is self-pollinated, however segregating genotypes have been identified, indicating the existence of partial outcrossing.

One aim of a plant breeder is to combine desirable traits in a single variety. Such desirable traits may include any trait deemed beneficial by a grower and/or consumer, which include greater yield, resistance to insects or disease, tolerance to environmental stress, and nutritional value. Additionally, there are chemical compounds known to be isolated from *Clitoria ternatea* and these include triterpenoids, flavonol glycosides, steroids, and anthocyanins. Total anthocyanin level in particular, is an example of a desirable trait. Therefore, it is of great interest of breeders to select and develop butterfly pea plants that have increased anthocyanin content resulting in superior varieties.

So far, breeding efforts have provided a number of useful butterfly pea lines with beneficial traits, however, there remains a great need in the art or new lines with further improved traits. Thus, there is a need for new butterfly pea varieties with improved traits, particularly butterfly pea varieties with high anthocyanin levels.

SUMMARY OF THE INVENTION

The objective of the invention was to develop a butterfly pea variety with a high anthocyanin content.

In one aspect the present invention provides seed of a butterfly pea variety, designated SXT BFP, having been deposited under Accession Number PTA-127280, a plant, or a part thereof, produced by growing said seed. The invention also provides methods and compositions relating to plants and plant parts, such as pollen, flowers, seeds, pods, leaves, stems and progenies of butterfly pea variety SXT BFP.

In another aspect, the invention provides a composition comprising a seed of butterfly pea variety SXT BFP comprised in plant seed growth media. In certain embodiments, the plant seed growth media is a soil or synthetic cultivation medium. In specific embodiments, the growth medium maybe be comprised in a container or may, for example, be soil in a field. Plant seed growth media are well known to those of skill in the art and include, but are in no way limited to, soil or synthetic cultivation medium.

In a further aspect of the invention relates to a tissue culture of regenerable cells of the butterfly pea variety SXT BFP, as well as plants regenerated there from, wherein the regenerated butterfly pea plant is capable of expressing all the morphological and physiological characteristics of a plant grown from the butterfly pea seed designated SXT BFP.

Still yet another aspect of the invention relates to a first generation ($F_1$) hybrid butterfly pea seed produced by crossing a plant of the butterfly pea variety SXT BFP to a second butterfly pea plant. Also included in the invention are the $F_1$ hybrid butterfly pea plants grown from the hybrid seed produced by crossing the butterfly pea variety SXT BFP to a second butterfly pea plant.

Still yet another aspect of the invention is a method of producing butterfly pea seeds comprising crossing a plant of the butterfly pea variety SXT BFP to any second butterfly pea plant, including itself or another plant of the variety SXT BFP. In particular embodiments of the invention, the method of crossing comprises the steps of a) planting seeds of the butterfly pea variety SXT BFP; b) cultivating butterfly pea plants resulting from said seeds until said plants bear flowers; c) allowing fertilization of the flowers of said plants; and d) harvesting seeds produced from said plants.

Still yet another aspect of the invention is a method of producing hybrid butterfly pea seeds comprising crossing the butterfly pea variety SXT BFP to a second, distinct butterfly pea plant that is non-isogenic to the butterfly pea variety SXT BFP. In particular embodiments of the invention, the crossing comprises the steps of a) planting seeds of butterfly pea variety SXT BFP and a second, distinct butterfly pea plant, b) cultivating the butterfly pea plants grown from the seeds until the plants bear flowers; c) cross-pollinating a flower on one of the two plants with the pollen of the other plant; and d) harvesting the seeds resulting from the cross-pollinating.

Still yet another aspect of the invention is a method for developing a butterfly pea plant in a butterfly pea breeding program comprising: obtaining a butterfly pea plant, or its parts, of the variety SXT BFP; and b) employing said plant or parts as a source of breeding material using plant breeding techniques. In the method, the plant breeding techniques may be selected from the group consisting of recurrent selection, mass selection, bulk selection, backcrossing, pedigree breeding, and genetic marker-assisted selection. In certain embodiments of the invention, the butterfly pea plant of variety SXT BFP is used as the male or female parent.

Still yet another aspect of the invention is a method of producing a butterfly pea plant derived from the butterfly pea variety SXT BFP, the method comprising the steps of: (a) crossing a plant of the butterfly pea variety SXT BFP with a second butterfly pea plant to produce a progeny plant that is derived from butterfly pea variety SXT BFP; and (b) crossing the progeny plant with itself or a second plant to produce a progeny plant of a subsequent generation that is derived from a plant of the butterfly pea variety SXT BFP. In one embodiment of the invention, the method further comprises: (c) crossing the progeny plant of a subsequent generation with itself or a second plant to produce a progeny plant of a further subsequent generation that is derived from a plant of the butterfly pea variety SXT BFP; and (d) repeating step (c), in some embodiments, at least 2, 3, 4 or more additional generations to produce an inbred butterfly pea plant that is derived from the butterfly pea variety SXT BFP. The invention still further provides a butterfly pea plant produced by this and the foregoing methods.

In another embodiment of the invention, the method of producing a butterfly pea plant derived from the butterfly pea variety SXT BFP further comprises: (a) crossing the butterfly pea variety SXT BFP derived butterfly pea plant with itself or another butterfly pea plant to yield additional butterfly pea variety SXT BFP derived progeny butterfly pea seed; (b) growing the progeny butterfly pea seed of step (a) under plant growth conditions to yield additional butterfly pea variety SXT BFP derived butterfly pea plants; and (c) repeating the crossing and growing steps of (a) and (b) to generate further butterfly pea variety SXT BFP derived butterfly pea plants. In specific embodiments, steps (a) and (b) may be repeated at least 1, 2, 3, 4, or 5 or more times as desired. The invention still further provides a butterfly pea plant produced by this and the foregoing methods.

DETAILED DESCRIPTION OF THE DRAWINGS

FIG. 1 shows a table of the USDA descriptors for a field trial of SXT BFP and a panel of USDA butterfly pea varieties.

FIG. 2 shows the USDA descriptors for flower color, petal number, leaf shape, and growth habit that were used to characterize the SXT BFP and a panel of USDA butterfly pea varieties.

DETAILED DESCRIPTION OF THE INVENTION

The invention provides methods and composition relating to plants, seeds, and derivatives of the butterfly pea variety SXT BFP.

One aspect of the current invention concerns methods for crossing the butterfly pea variety SXT BFP with itself or a second plant and the seeds and plants produced by such methods. These methods can be used for propagation of the butterfly pea variety SXT BFP or can be used to produce hybrid butterfly pea seeds and the plants grown there from. Hybrid butterfly pea plants can be used by breeders in the commercial production of butterfly pea products or may be advanced in certain breeding protocols for the production of novel butterfly pea varieties. A hybrid plant can also be used as a recurrent parent at any given stage in a backcrossing protocol during the production of a single locus conversion of the butterfly pea variety SXT BFP. Butterfly pea variety SXT BFP is well suited to the development of new varieties based on the elite nature of the genetic background of the variety. In selecting a second plant to cross with SXT BFP for the purpose of developing novel butterfly pea varieties, it will typically be desired to choose those plants that either themselves exhibit one or more selected characteristics or that exhibit the characteristic(s) when in hybrid combination. Examples of potentially selected characteristics include increased anthocyanin content, increased flower size, multiple petals, broad environmental adaptation, and insect and pest resistance, and resistance to bacterial, fungal, or viral disease.

Choice of breeding or selection methods depends on the mode of plant reproduction, the heritability of the trait(s) being improved, and the type of variety used commercially (e.g., $F_1$ hybrid variety, pure line variety, etc.). For highly heritable traits, a choice of superior individual plants evaluated at a single location will be effective; whereas, for traits with low heritability, selection should be based on mean values obtained from replicated evaluations of families of related plants. Popular selection methods commonly include pedigree selection, modified pedigree selection, mass selection, recurrent selection and backcrossing.

The complexity of inheritance influences the choice of the breeding method. Backcross breeding is used to transfer one or a few genes for a highly heritable trait into a desirable variety. This approach has been used extensively (Bowers et al., *Crop Sci.*, 32(1):67-72, 1992; Nickell and Bernard, *Crop Sci.*, 32(3):835, 1992). Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross. Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input, e.g., per year, per dollar expended, etc.

Promising advanced breeding lines are thoroughly tested and compared to appropriate standards in environments that are representative of the commercial target area(s) for generally three or more years. The best lines are candidates for new commercial varieties. Those still deficient in a few traits may be used as parents to produce new populations for further selection.

These processes, which lead to the final step of marketing and distribution, may take as much as 8 to 12 years from the time the first cross is made. Therefore, development of new varieties is a time-consuming process that requires precise forward planning, efficient resource utilization, and minimal direction changes.

Identifying individuals that are genetically superior is a difficult task because the true genotypic value for most traits can be masked by other confounding traits or environmental factors. One method of identifying a superior plant is observing its performance relative to other experimental plants and one or more widely grown standard varieties. Single observations are generally inconclusive, while replicated observations provide a better estimate of genetic worth.

The goal of plant breeding is to develop new, unique, and superior butterfly pea varieties and hybrids. The breeder initially selects and crosses two or more parental lines. This is generally followed by repeated selfing and selection, which produces many new genetic combinations. Each year, the plant breeder selects the germplasm to advance to the next generation. This germplasm is grown under unique and different geographical, climatic, and soil conditions, and further selections are then made during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a gross and general fashion. The same breeder cannot produce the same variety twice by using the exact same original parents and the same selection techniques. This unpredictability results in the expenditure of large amounts of research monies to develop superior new butterfly pea varieties.

Pedigree breeding and recurrent selection breeding methods are used to develop varieties from breeding populations.

Breeding programs combine traits from two or more varieties or various broad-based sources into breeding pools from which varieties are developed by selfing and selection of phenotypes. The new varieties are evaluated to determine which have commercial potential.

Pedigree breeding is commonly used for the improvement of self-pollinating crops. Two parents which possess favorable, complementary traits are crossed to produce $F_1$ progeny. An $F_2$ population is then produced by selfing one or several $F_1$ plants. Selection of the best individuals may begin in the $F_2$ population or later depending upon the breeder's objectives; then, beginning in the $F_3$ generation, the best individuals in the best families can be selected. Replicated testing of families can begin in the $F_3$ or $F_4$ generations to improve the effectiveness of selection for traits of low heritability. At an advanced stage of inbreeding (i.e., the $F_6$ and $F_7$ generations), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population from which further cycles of selection are continued.

Backcross breeding has been used to transfer genetic loci for simply inherited or highly heritable traits into a homozygous variety that is used as the recurrent parent. The source of the trait to be transferred is called the donor or non-recurrent parent. The resulting plant is expected to have the attributes of the recurrent parent and the trait transferred from the donor parent. After the initial cross, individuals possessing the phenotype of the donor parent are selected and repeatedly crossed, i.e., backcrossed, to the recurrent parent. The resulting plant is expected to have the attributes of the recurrent parent (i.e., variety) and the desirable trait transferred from the donor parent. The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which the lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed. Descriptions of other breeding methods that are commonly used for different traits and crops can be found in one of several reference books (e.g., Allard, "Principles of Plant Breeding," John Wiley & Sons, NY, University of California, Davis, Calif., 50-98, 1960; Simmonds, "Principles of Crop Improvement," Longman, Inc., NY, 369-399, 1979; Sneep et al., "Plant breeding perspectives," Wageningen (ed.), Centre for Agricultural Publishing and Documentation, 1979.

Proper testing should detect any major faults and establish the level of superiority or improvement over current varieties. In addition to showing superior performance, there must be a demand for a new variety that is compatible with industry standards or which creates a new market. The introduction of a new variety will incur additional costs to the seed producer, the grower, processor, and consumer. The testing preceding release of a new variety should take into consideration research and development costs as well as the technical superiority of the final variety. For seed-propagated varieties, it must be feasible to produce seed easily and economically. In addition to phenotypic observations, a plant can also be identified by its genotype. The genotype of a plant can be characterized through a molecular marker profile, which can identify plants of the same variety or a related variety, can identify plants and plant parts which are genetically superior as a result of an event comprising a backcross conversion, which can be used to determine or validate a pedigree. Such molecular marker profiling can be accomplished using a variety of techniques including, but not limited to, restriction fragment length polymorphism (RFLP), amplified fragment length polymorphism (AFLP), sequence-tagged sites (STS), randomly amplified polymorphic DNA (RAPD), arbitrarily primed polymerase chain reaction (AP-PCR), DNA amplification fingerprinting (DAF), sequence characterized amplified regions (SCARs), variable number tandem repeat (VNTR), short tandem repeat (STR), single feature polymorphism (SFP), simple sequence length polymorphism (SSLP), restriction site associated DNA, allozymes, isozyme markers, single nucleotide polymorphisms (SNPs), or simple sequence repeat (SSR) markers, also known as microsatellites (Gupta et al., 1999; Korzun et al., 2001). Various types of these markers, for example, can be used to identify individual varieties developed from specific parent varieties, as well as cells or other plant parts thereof. For example, see Berry et al. (2003) "Assessing Probability of Ancestry Using Simple Sequence Repeat Profiles: Applications to Maize Inbred Lines and Butterfly pea Varieties" *Genetics* 165(1):331-342, each of which are incorporated by reference herein in their entirety.

In some examples, one or more markers may be used to characterize and/or evaluate a butterfly pea variety. Particular markers used for these purposes are not limited to any particular set of markers but are envisioned to include any type of marker and marker profile that provides a means for distinguishing varieties. One method of comparison may be to use only homozygous loci for butterfly pea variety SXT BFP. Primers and PCR protocols for assaying these and other markers, in addition to being used for identification of butterfly pea variety SXT BFP, as well as plant parts and plant cells of butterfly pea variety SXT BFP, a genetic profile may be used to identify a butterfly pea plant produced through the use of butterfly pea variety SXT BFP or to verify a pedigree for progeny plants produced through the use of butterfly pea variety SXT BFP. A genetic marker profile may also be useful inbreeding and developing backcross conversions.

In an embodiment, the present invention provides a butterfly pea plant characterized by physiological data obtained from a representative sample of said variety deposited with the American Type Culture Collection (ATCC). Thus, plants, seeds, or parts thereof, having all or essentially all of the morphological and physiological characteristics of butterfly pea variety SXT BFP are provided. Further provided is a butterfly pea plant formed by the combination of the disclosed butterfly pea plant or plant cell with another butterfly pea plant or cell and comprising the homozygous alleles of the variety.

In some examples, a plant, a plant part, or a seed of butterfly pea variety SXT BFP may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like.

A molecular profile may also be a nucleic acid sequence profile, and/or a physical map. A phenotypic profile may include, but is not limited to, a protein expression profile, a metabolic profile, an mRNA expression profile, and the like. One means of performing genetic marker profiles is using SSR polymorphisms that are well known in the art. A marker system based on SSRs can be highly informative in linkage analysis relative to other marker systems, in that multiple alleles may be present. Another advantage of this type of marker is that through use of flanking primers, detection of SSRs can be achieved, for example, by using the polymerase chain reaction (PCR), thereby eliminating the need for labor-intensive Southern hybridization. PCR detection maybe performed using two oligonucleotide primers flanking the polymorphic segment of repetitive DNA to amplify the SSR region. Following amplification, markers can be scored by electrophoresis of the amplification products. Scoring of marker genotype is based on the size of the amplified fragment, which correlates to the number of base pairs of the fragment. While variation in the primer used or in the laboratory procedures can affect the reported fragment size, relative values should remain constant regardless of specific primer or laboratory used.

When comparing varieties, it may be beneficial to have all profiles performed in the same lab. A genotypic profile of butterfly pea variety SXT BFP can be used to identify a plant comprising butterfly pea variety SXT BFP as a parent, since such plants will comprise the same homozygous alleles as variety SXT BFP. Because the butterfly pea variety is essentially homozygous at all relevant loci, most loci should have only one type of allele present. In contrast, a genetic marker profile of an F1 progeny should be the sum of those parents, e.g., if one parent was homozygous for allele X at a particular locus, and the other parent homozygous for allele Y at that locus, then the $F_1$ progeny will be XY (heterozygous) at that locus. Subsequent generations of progeny produced by selection and breeding are expected to be of genotype XX (homozygous), YY (homozygous), or XY (heterozygous) for that locus position. When the $F_1$ plant is selfed or sibbed for successive filial generations, the locus should be either X or Y for that position.

A genotypic profile of variety SXT BFP also can be used to identify essentially derived varieties and other progeny varieties developed from the use of variety SXT BFP, as well as cells and other plant parts thereof. Plants of the invention include any plant having at least 90%, 91%, 92%, 93%, 94%, 95%, 96%, 97%, 98%, 99%, 99.5%, or 99.9% of the markers in the genotypic profile, and that retain 90%, 91%, 92%, 93%, 94%, 95%, 96%, 97%, 98%, 99%, 99.5%, or 99.9% of the morphological and physiological characteristics of variety SXT BFP when grown under the same conditions. Such plants may be developed using markers well known in the art. Progeny plants and plant parts produced using variety SXT BFP may be identified, for example, by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from butterfly pea variety SXT BFP, as measured by either percent identity or percent similarity. Such progeny may be further characterized as being within a pedigree distance of variety SXT BFP, such as within 1, 2, 3, 4, or 5 or less crosspollinations to a butterfly pea plant other than variety SXT BFP, or a plant that has variety SXT BFP as a progenitor. Unique molecular profiles may be identified with other molecular tools, such as SNPs and RFLPs.

Any time the butterfly pea variety SXT BFP is crossed with another, different, variety, first generation ($F_1$) butterfly pea progeny are produced. The hybrid progeny are produced regardless of characteristics of the two varieties produced. As such, an $F_1$ hybrid butterfly pea plant may be produced by crossing SXT BFP with any second butterfly pea plant. The second butterfly pea plant may be genetically homogeneous (e.g., inbred) or may itself be a hybrid. Therefore, any $F_1$ hybrid butterfly pea plant produced by crossing butterfly pea variety SXT BFP with a second butterfly pea plant is a part of the present invention.

Further Embodiments of the Invention

In certain aspects of the invention, plants of butterfly pea variety SXT BFP are modified to include at least a first heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. By essentially all of the morphological and physiological characteristics, it is meant that the characteristics of a plant are recovered that are otherwise present when compared in the same environment, other than occasional variant traits that might arise during backcrossing.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a butterfly pea plant is obtained wherein essentially all of the morphological and physiological characteristics of the recurrent parent are recovered in the converted plant, in addition to the transferred locus from the nonrecurrent parent.

The selection of a suitable recurrent parent is an important step for a successful backcrossing procedure. The goal of a backcross protocol is to alter or substitute a trait or characteristic in the original variety. To accomplish this, a locus of the recurrent variety is modified or substituted with the desired locus from the nonrecurrent parent, while retaining essentially all of the rest of the genome of the original variety, and therefore the morphological and physiological constitution of the original variety. The choice of the particular nonrecurrent parent will depend on the purpose of the backcross; one of the major purposes is to add an agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many traits have been identified that are not regularly selected for in the development of a new inbred but that can be improved by backcrossing techniques. These traits include, but are not limited to, increased anthocyanin content, increased flower size, multiple petals, broad environmental adaptation, and insect and pest resistance, and resistance to bacterial, fungal, or viral disease. These comprise genes generally inherited through the nucleus.

Selection of butterfly pea plants for breeding is not necessarily dependent on the phenotype of a plant and instead can be based on genetic investigations. For example, one may utilize a suitable genetic marker that is closely associated with a trait of interest. One of these markers may therefore be used to identify the presence or absence of a trait in the offspring of a particular cross, and hence may be used in selection of progeny for continued breeding. This technique may commonly be referred to as marker assisted selection. Any other type of genetic marker or other assay that is able to identify the relative presence or absence of a trait of interest in a plant may also be useful for breeding purposes. Procedures for marker assisted selection applicable to the breeding of butterfly pea are well known in the art. Such methods will be of particular utility in the case of recessive traits and variable phenotypes, or when conventional assays may be more expensive, time consuming or otherwise disadvantageous. Genetic markers that could be used in accordance with the invention include, but are not necessarily limited to, Simple Sequence Length Polymorphisms (SSLPs) (Williams et al., *Nucleic Acids Res.*, 18:6531-6535,1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (European Patent Application Publication No. EP0534858, incorporated herein by reference in its entirety), and Single Nucleotide Polymorphisms (SNPs) (Wang et al., *Science*, 280: 1077-1082, 1998).

Deposit Information: In accordance with 37 C.F.R. 1.801-1.809, a representative sample of seeds of Butterfly Pea Variety SXT BFP has been deposited with the American Type Culture Collection (ATCC), 10801 University Boulevard, Manassas, VA 20110-2209 on Mar. 7, 2022, and has been assigned Accession No. PTA-127280.

EXAMPLES

Example 1

Development of SXT BFP

The variety SXT BFP was developed from plant selection and line purification trials from *Clitoria ternatea* germplasm collected from the Philippines, Indonesia and Thailand and evaluated for adaptation, disease and pest resistance, calyx size, petal color, petal number, petal size and petal yield in 8-10 locations in the Philippines and 2-3 locations in Indonesia for the 2017-2019. Butterfly pea plant selection and line purification was performed in a nursery in the Philippines by roguing undesirable butterfly pea plants until a homogeneous population exhibiting all the desirable traits for a botanical colorant was identified. Briefly, selected butterfly pea plants were tagged and allowed to undergo selfing and seeds of these butterfly pea plants were used to generate the next generation of butterfly pea plants. Two to three cycles of butterfly pea plant selection were performed per year to develop the butterfly pea variety SXT BFP.

FIG. 1 shows a table of the USDA descriptors for a field trial of SXT BFP and a panel of USDA butterfly pea varieties. FIG. 2 shows the USDA descriptors for flower color, petal number, leaf shape, and growth habit that were used to characterize the SXT BFP and a panel of USDA butterfly pea varieties. The values are mean values. Dried petal samples of the selected individuals were then sent to Italy for color quality testing. Seed increase was performed on selected individuals that constitute the SXT BFP line.

Aside from this initial population, breeding for superior butterfly pea lines are currently ongoing in the Indonesia and the Philippines with the goal of producing lines with the high anthocyanin content, multiple petals, increased yield, improved pest and disease resistance and broad climate adaptation.

Example 2

DNA Genotyping for Parental Selection

Ten (10) trifoliate leaves will be collected from each of the plant from each accession. Dry the leaves in the oven at 60° C. overnight. Tissue samples will be shipped to University of Georgia for DNA analysis.

Genetic diversity analysis will be performed using the soy SNP marker panel and parents will be selected based on genetic diversity scores for all the targets traits.

For population development, crosses for genetic mapping will be attempted on selected parental combinations.

Each mapping population will consist of 150 $F_2$ individuals, which means multiple $F_1$ crosses have to be developed. Identity of individual plants will be maintained to allow tracking to original $F_1$ seeds and parental lines. QTL mapping and analysis will be performed.

What is claimed:

1. A plant of butterfly pea variety SXT BFP, wherein representative seed of said butterfly pea variety have been deposited under ATCC Accession No. PTA-127280.

2. A plant part of the plant of claim 1, wherein the plant part comprises at least one cell of said plant.

3. A seed of butterfly pea variety SXT BFP, wherein representative seed of said butterfly pea variety have been deposited under ATCC Accession No. PTA-127280.

4. A method of producing butterfly pea seed, the method comprising crossing the plant of claim 1 with itself or a second butterfly pea plant to produce said butterfly pea seed.

5. The method of claim 4, the method further comprising crossing the plant of butterfly pea variety SXT BFP with a second, non-isogenic butterfly pea plant to produce said butterfly pea seed.

6. An $F_1$ butterfly pea seed produced by the method of claim 5.

7. A butterfly pea plant produced by growing the $F_1$ butterfly pea seed of claim 6.

8. A composition comprising the seed of claim 3 comprised in plant seed growth media.

9. The composition of claim 8, wherein the plant seed growth media is soil or a synthetic cultivation medium.

10. A plant of butterfly pea variety SXT BFP further comprising a single locus conversion, wherein said plant otherwise comprises all of the morphological and physiological characteristics of said butterfly pea variety when grown under the same environmental conditions, and wherein representative seed of said butterfly pea variety have been deposited under ATCC Accession No. PTA-127280.

11. A seed that produces the plant of claim 10.

12. The seed of claim 11, wherein the single locus confers a trait selected from the group consisting of increased anthocyanin content, increased flower size, multiple petals, broad environmental adaptation, and insect and pest resistance, and resistance to bacterial, fungal, or viral disease.

13. The method of claim 5, the method further comprising:

a. crossing a plant grown from said butterfly pea seed with itself or a different butterfly pea plant to produce seed of a progeny plant of a subsequent generation;
b. growing a progeny plant of a subsequent generation from said seed of a progeny plant of a subsequent generation and crossing the progeny plant of a subsequent generation with itself or a second plant to produce seed of a progeny plant of a further subsequent generation; and
c. repeating step (b) with sufficient inbreeding to produce seed of an inbred butterfly pea plant that is derived from butterfly pea variety SXT BFP.

14. The method of claim 13, the method further comprising crossing a plant grown from said seed of an inbred butterfly pea plant that is derived from butterfly pea variety SXT BFP with a non-isogenic plant to produce seed of a hybrid butterfly pea plant that is derived from butterfly pea variety SXT BFP.

15. A method of producing a commodity plant product, the method comprising producing the commodity plant product from the plant of claim 1.

16. The method of claim 15, wherein the commodity plant product is anthocyanin.

\* \* \* \* \*